(12) United States Patent
Recknor et al.

(10) Patent No.: US 7,556,045 B1
(45) Date of Patent: Jul. 7, 2009

(54) SYSTEM AND METHOD FOR OSTEOPOROSIS ASSESSMENT

(75) Inventors: Chris Recknor, Gainesville, GA (US); Stephanie Grant, Gainesville, GA (US)

(73) Assignee: Chris Recknor, M.D. P.C., Gainesville, GA (US)

( * ) Notice: Subject to any disclaimer, the term of this patent is extended or adjusted under 35 U.S.C. 154(b) by 796 days.

(21) Appl. No.: 11/002,374

(22) Filed: Dec. 2, 2004

(51) Int. Cl.
*A61B 19/00* (2006.01)
(52) U.S. Cl. ..................................................... 128/898
(58) Field of Classification Search ................. 128/898; 600/449; 378/54
See application file for complete search history.

(56) References Cited

U.S. PATENT DOCUMENTS

| | | | | |
|---|---|---|---|---|
| 6,385,283 | B1 * | 5/2002 | Stein et al. | 378/54 |
| 6,740,041 | B2 * | 5/2004 | Faulkner et al. | 600/449 |

OTHER PUBLICATIONS

M. Moro, A. T. Hecker, M. L. Bouxsein, E. R. Myers; "Failure Load of Thoracic Vertebrae Correlates with Lumbar Bone Mineral Density Measured by DXA"; Calcified Tissue International; 1995; 56:206-209; Springer-Verlag New York, Inc.

E. N. Ebbesen, J. S. Thomsen, H. Beck-Nielsen, H. J. Nepper-Rasmussen, and Li Mosekilde: Lumbar Vertebral Body Compressive Strength Evaluated by Dual-Energy X-ray Absorptiometry, Quantitative Computed Tomography, and Ashing; Bone; vol. 25, No. 6; Dec. 1999:713-724; Elsevier Science, Inc.

Yunbo Duan, Ego Seeman and Charles H. Turner; "The Biomechanical Basis of Vertebral Body Fragility in Men and Women"; Journal Of Bone And Mineral Research; vol. 16, No. 12, 2001; American Society for Bone and Mineral Research.

E. R. Myers and S. E. Wilson; "Biomechanics of Osteoporosis and Vertebral Fracture"; Spine; vol. 22, No. 24S; pp. 25S-31S, 1997 Lippincott-Raven Publishers.

* cited by examiner

*Primary Examiner*—William H. Matthews
(74) *Attorney, Agent, or Firm*—Withers & Keys, LLC (57) ABSTRACT

An osteoporosis assessment system and method. The system and method generally include an input device that can be a computer that can be further connected to a network. The system can therefore be web-based. The system receives patient data and data related to osteoporosis. The method is implemented to correlate the patient data and the osteoporosis data and output is generated that personalizes the osteoporosis data to the patient based on the valued activities of the patient, so that the patient can understand his or her personal fracture risk assessment, therapy needs determination and therapy progress measurement. Therapy and treatment recommendations can also be generated.

29 Claims, 9 Drawing Sheets

Patient Name: _______________________   Date: _______________
Height _____________________________   Weight _____________

Physical Symptoms Assessment

| | | | |
|---|---|---|---|
| Pain: | Pre-test: ___/10 | Post-test: ___/10 | |
| Dizziness: | Pre-test: ___/10 | Post-test: ___/10 | |
| Posture: | Lumbosacral: ___ | Lordosis: ___ | Kyphosis: ___ |

Valued Activities Checklist

| Activity | √ | Activity | √ |
|---|---|---|---|
| *Basic Activities of Daily Living* | | Caring for Pet | |
| Getting In/Out of Bed | | Caregiving | |
| Bathing/Showering | | Mowing the Lawn | |
| Brushing Teeth | | Raking | |
| Eating | | Other ___________ | |
| Dressing | | *Leisure Activities* | |
| Grooming | | Running | |
| Physically Intimate Relationship | | Swimming | |
| Resting/Sleeping | | Fishing | |
| Other ___________ | | Shopping | |
| *Instrumental Activities of Daily Living* | | Decorating | |
| Washing Dishes | | Dancing | |
| Meal Preparation | | Tennis | |
| Cooking | | Golfing | |
| Getting the Mail | | Bowling | |
| Laundry | | Walking | |
| Ironing | | Hiking | |
| Talking on Phone | | Community Leisure | |
| Using Computer | | Biking | |
| Household Maintenance | | Yard Games | |
| Grocery Shopping | | Feeding the Birds | |
| Taking out Trash | | Gardening | |
| Load/Unload Dishwasher | | Woodworking | |
| Reaching into Cabinet/Closet | | Hunting | |
| Making/Changing Bed Sheets | | Exercising | |
| Driving | | Horseback Riding | |
| Getting Gas | | Canoeing/Boating | |
| Car Passenger | | Traveling | |
| Going to the Doctor | | Other ___________ | |
| Child Care | | *Productive Activities: Please List:* | |
| Carrying a Purse | | | |
| Cleaning Bathtub | | Sitting Tasks on the Job/Volunteer | |
| Light Cleaning | | Standing Tasks on the Job/Volunteer | |
| Sweeping | | | |
| Vacuuming | | *Other* | |
| Mopping | | Sitting and Watching | |
| Car Maintenance | | Sitting and Doing | |
| | | Other ___________ | |

Safe Functional Mobility Subtest
Scoring Sheet

| TASKS | SPINAL COMPRESSION FORCES DOMAIN | BALANCE/ COORDINATION DOMAIN | UPPER BODY STRENGTH DOMAIN | LOWER STRENGTH/ TRUNK STABILITY DOMAIN | UPPER BODY FLEXIBILITY DOAMIN | LOWER BODY FLEXIBILITY DOMAIN |
|---|---|---|---|---|---|---|
| Pour | Carried: Close = 1 Away = 0 Turning Method: No Twist = 1 Twist = 0 Reaching Method: Squat/Kneel/ Adaptation = 1 Bend at Spine = 0    3 | Turn: No LOB = 2 Unsteady = 1 LOB = 0 Pour: No LOB = 2 Unsteady = 1 LOB = 0    4 | Wt. Carried: >=5lb = 2 5 lb = 1 <5lb = 0    2 | | | |
| Footwear | Method: Bend Knee/ Adaptation = 1 Bend at Spine = 0    1 | | | | | ROM: Full = 1 < Full = 0    1 |
| Newspaper | Method: Squat/Kneel/ Adaptation = 1 Bend at Spine = 0    1 | Method: No LOB = 2 Unsteady = 1 LOB = 0    2 | | Use of Legs: Squat/Kneel = 2 Partial Squat /Kneel = 1 Bend at Spine = 0    2 | | Use of Legs: Squat/Kneel = 2 Partial Squat /Kneel = 1 Bend at Spine = 0    2 |
| Reach-Lift | Method: Flat footed/ Adaptation = 1 Tip toes = 0    1 | Method: No LOB = 2 Unsteady = 1 LOB = 0    2 | Wt. Lifted: >=5lb = 2 5 lb = 1 <5lb = 0    2 | | ROM: ≥ 90° = 1 < 90° = 0    1 | |
| Sweep | Method: Squat/Kneel/ Adaptation = 1 Bend at Spine = 0    1 | Method: No LOB = 2 Unsteady = 1 LOB = 0    2 | | | | |
| Washer | Reach Method: Golfer's Reach/ Adaptation = 1 Bend at Spine = 0    1 | | | | ROM: ≥ 90° = 1 < 90° = 0    1 | |
| Dryer | Method: Squat/Kneel / Adaptation = 1 Bend at Spine = 0 Twist: Body as unit/ Adaptation = 1 Twists Spine = 0    2 | | Basket Lift: > 5 lb = 2 5 lb = 1 < 5 lb = 0    2 | Use of Legs: Squat/Kneel = 2 Partial Squat /Kneel = 1 Bend at Spine = 0    2 | ROM: ≥ 90° = 1 < 90° = 0    1 | Use of Legs: Squat/Kneel = 2 Partial Squat /Kneel = 1 Bend at Spine = 0    2 |
| Sit to Floor | Method: Squat/Kneel/ Adaptation = 1 Bend at Spine = 0    1 | Method: No LOB = 2 Unsteady = 1 LOB = 0 Sit: No use of Chair= 1 Chair as Assist =0    3 | | Use chair: No = 1 Yes = 0    1 | | Sits LEs straight: Yes = 1    1 No = 0 |

| TASKS | SPINAL COMPRESSION FORCES DOMAIN | BALANCE/ COORDINATION DOMAIN | UPPER BODY STRENGTH DOMAIN | LOWER STRENGTH/ TRUNK STABILITY DOMAIN | UPPER BODY FLEXIBILITY DOAMIN | LOWER BODY FLEXIBILITY DOMAIN |
|---|---|---|---|---|---|---|
| Carry-Climb | Attempt >10lb: No = 1 Yes = 0 Carried Wt Evenly: Yes = 1 No = 0    2 | Method: No LOB = 2 Unsteady/Poor Head Turns = 1 LOB = 0 Climb: No Rail/Guide = 2 Rail as Assist = 1 No Climb - 0 Feet Per Step: One = 2 Two = 1 No Climb =0    4 | Wt. Carried: >=5lb = 2 5lb = 1 <5lb = 0    2 | Climb Stairs: Yes = 1 No = 0    1 | ROM: ≥ 90° = 1 < 90° = 0    1 | |
| Night Walk | | Balance (light): No LOB = 2 Unsteady = 1 LOB = 0 Balance (no light): No LOB = 2 Unsteady = 1 LOB = 0    4 | | | | |
| Domain Total Scores | __/13 = __% | __/23= __% | __/8= __% | __/6= __% | __/4= __% | __/6= __% |
| | SAFETY SCORE __/36 = ____% | | PHYSICAL PERFORMANCE SCORE __/47 = ____% | | | |

Fig. 5

THERAPY IF THEN DOCUMENT

IF LESS THAN (100%) IN SPINAL COMPRESSION FORCES, THEN:

Instruction in Bone Safe Motion is indicated to prevent vertebral fractures in the future.

IF LESS THAN (100%) IN BALANCE AND COORDINATION, THEN:

Balance testing and retraining is indicated to prevent falls in the future.

Fall prevention and protection programming is recommended including: hip protectors, home safety and community safety concerns.

IF UE FLEXIBILITY IS IMPAIRED (WHEN OVERHEAD REACHING IS IMPAIRED), THEN:

Upper extremity range of motion program may be indicated to improve flexibility.

Recommend patient set up items at shoulder height.

............AND BALANCE AND COORDINATION IS NORMAL:
Recommend use of step stool when placing items on higher shelves/cabinets.

............AND BALANCE AND COORDINATION IS IMPAIRED:
Recommend use of reacher to obtain light items on higher shelves/cabinets

IF LE FLEXIBILITY IS IMPAIRED (WHEN SQUATING/KNEELING IS IMPAIRED), THEN:

Long handled devices, such as a reacher, long handled dustpan, long handled sponge, sock aide, or long handled shoe horn, may be appropriate to compensate for decreased range of motion.

Lower extremity range of motion program is indicated to improve flexibility.

IF UE STRENGTH IS IMPAIRED (WHEN UNABLE TO LIFT > 5 POUNDS), THEN:

Upper extremity strengthening program is recommended.

Recommend patient set up items at or below shoulder height.

IF LE STRENGTH IS IMPAIRED (WHEN UNABLE TO STAND FROM KNEELING/SQUATING), THEN:

Recommend patient set up items at or above waist height.

Lower extremity strengthening program is indicated.

Long handled devices, such as a reacher, long-handled dust pan, etc.

Instruction in need to use golfer's reach when reaching for items in low places to minimize spinal compression forces when squatting and kneeling are not possible ............AND BALANCE AND COORDINATION IS IMPAIRED:
Recommend use of assistive device for walking to prevent falls

Activity Risk Report

You have just completed the Bone Safety Evaluation, which has provided us with information regarding how you move during everyday tasks. The following chart is a list of activites in which you stated you are currently participating. Based on your bone density test and your performance on the Bone Safety Evaluation, an "X" is placed beside each activity to indicate that there is an increased risk for excessive stress on your bones given your present balance condition and movement patterns.

| Activity | Fall Risk | Spine Risk |
|---|---|---|
| Getting In/Out of Bed | X | X |
| Showering | X | X |
| Dressing | X | X |
| Grooming |  | X |
| Sleeping on side |  | X |
| Dishes | X | X |
| Cooking | X | X |
| Grocery Shopping | X | X |
| Taking Out the Trash | X | X |
| Make/Change Bed Sheets | X | X |
| Driving | X | X |
| Carrying a Purse |  | X |
| Cleaning the Shower | X | X |
| Sweeping | X | X |
| Mopping | X | X |
| Dusting | X | X |
| Sitting and Watching |  | X |
| Shopping | X | X |
| Walking | X | X |
| Exercising (climbs stairs) | X | X |

Fig. 8

Therapy Recommendation and Activity Modification Report

Based on Mrs. J's score on the SFM Domain of the BSE, the following recommendations and modifications are indicated.

SFM Sub Domain Scores:
- Spinal Compression Forces: 1/13
- Balance and Coordination: 15/21
- Upper Body Strength: 8/8
- Lower Body Strength: 5/10
- Upper Body Flexibility: 4/4
- Lower Body Flexibility: 5/10

Recommendations and Activity Modifications:
- Instruction in bone safe motion is indicated to prevent vertebral fractures in the future.
- Balance testing and retraining is indicated to prevent falls in the future.
- Fall prevention and protection programming is recommended including hip protectors, home safety and community safety concerns.
- Recommend patient set up items at or above waist height.
- Lower extremity strengthening program is indicated.
- Long handled devices, such as a reacher, long-handled dustpan, etc.
- Lower extremity range of motion program is indicated to improve flexibility.
- Instruction in need to use golfer's reach when reaching for items in low places to minimize spinal compression forces when squatting and kneeling are not possible.
- Recommend use of an assistive device for walking to prevent falls
- Long handled devices, such as a reacher, long handled dustpan, long handled sponge, sock aide, or long handled shoehorn, may be appropriate to compensate for decreased range of motion

Fig. 9

SYSTEM AND METHOD FOR OSTEOPOROSIS ASSESSMENT

BACKGROUND

I. Field of the Invention

The present invention relates generally to the field of medical evaluation tools and more particularly to a system and method for osteoporosis assessment, including fracture risk assessment, therapy needs determination and therapy progress measurement.

II. Description of the Related Art

It is estimated that 10 million Americans have osteoporosis and 44 million are at risk to develop osteoporosis because they have low bone density. Typically, many people with osteoporosis are not treated. The number of individuals who receive therapy treatment for prevention of osteoporosis or vertebral fractures is significantly less than the number of individuals referred for osteoporosis symptom management. Preventative therapy typically includes providing individuals with general osteoporosis information that simply includes recommendations not to twist or bend to prevent vertebral fractures. However, the information does not include any personalized information designed and catered to the activities in which the patient is presently engaged. No information is provided instructing patients how to modify their bodily motions to decrease risks associated with osteoporosis.

Historical approaches to fracture risk prediction begin with measuring bone mineral density (BMD) then modifying the BMD threshold for treatment depending on the presence or absence of other determined risk factors associated with osteoporosis (i.e., age, height, medications, caffeine intake, smoking, familial history, steroid use, calcium intake, age at menopause) (Ott, 2004; McLung, 1999; Cummings, 1995; Greenspan, 1994; Sorenson et al., 1996). Algorithms for lifetime fracture risk, near-term and future risk of fracture are prevalent in the literature (Miller et al., 2004; Cooper, 2001; Frost, 2001; Greenspan, 1994). There are few known fracture prediction models that incorporate BMD with biomechanical stresses associated with ordinary functional movement behavior (Myers and Wilson, 1997). However, no known model has been applied to clinical practice.

SUMMARY

The present invention provides a fracture risk prediction model for clinical application that addresses the concern of "functional risk for fracture". Functional risk for fracture is the risk for fracture associated with ordinary movements during daily life activities. A Bone Safety Evaluation (BSE) assesses these ordinary movements and modifies BMD threshold depending on the presence or absence of certain safe movement patterns. Given this purpose, the BSE can be used to determine if a patient's functional risk for fracture has changed due to various therapeutic protocols or interventions (i.e., occupational or physical therapy, group exercise or aquatic therapy).

In general, the invention features an osteoporosis assessment system and method. The system and method generally include an input device that can be a computer that can be further connected to a network. The system can therefore be web-based. The system receives patient data and data related to osteoporosis including fracture risk assessment, therapy needs determination and therapy progress measurement. The method is implemented to correlate the patient data and the osteoporosis data and output is generated that personalizes known risks associated with osteoporosis, such as fracture risks, so that a patient can use that knowledge to understand his or her personal fracture risk, therapy needs and therapy progress, based further on the valued activities of the patient. Therapy and treatment recommendations can also be generated. The method provides a systematic evaluation tool that evaluates a patient's movement patterns, including but not limited to, ability to maintain balance, avoid spinal compression force, demonstrate functional upper body strength, flexibility, demonstrate functional lower body and truck strength, demonstrate functional lower body flexibility, and correlates those movement patterns with known risks associated with osteoporosis to cater a specific program for a patient quantifying the risks associated with the activities in which the patient is presently engaged. Risk for fracture associated with movement during daily activity is known a functional fracture risk. Since persons with osteoporosis are often unaware of the negative effects that their movement patterns have on their bone safety, the method allows them to become aware. These movement patterns include spinal twisting and flexion and other dominant movement patterns used by an individual for performance of daily activities. Due to low bone density, high load that exceeds bone strength and/or cyclical loading on vertebral bodies, spinal twisting and flexion may increase the risk for fracture in individuals with osteoporosis. The disclosed methods assess the functional performance patterns of a person's daily life that can contribute to increased risk of fracture, such as twisting, flexion and balance. Because people have different interests such as gardening or playing tennis, a valued activities checklist assists in identifying the specific valued activities that a person wants and needs to do and a lifestyle change is effectively facilitated by the method. Individuals are provided with techniques for modifying or adapting movement patterns in order to decrease their risk for fractures. The techniques provided give the patient knowledge of the functional risk for fracture associated with their ordinary movements during their daily life activities.

In general, in one aspect, the invention features a method of osteoporosis assessment, including collecting patient data, collecting data related to osteoporosis, correlating the patient data and the osteoporosis data and generating output that relates the osteoporosis data and risks such as functional risk for fracture, specifically to the patient based on the valued activities of the patient. In general, a predetermined set of tasks are given to a patient to perform. The patient is observed performing those tasks and the analysis of those tasks are applied to the valued activities in which a patient regularly engages.

In one implementation, the patient data includes demographic data.

In another implementation, the patient data includes bone mineral density.

In another implementation, the patient data includes physical symptoms assessment data.

In another implementation, the physical symptoms assessment data includes posture data.

In another implementation, the posture data includes lumbosacral angle.

In another implementation, the posture data includes L1/T12.

In another implementation, the posture data includes T1/C7 data.

In another implementation, the physical symptoms assessment data includes pain and dizziness data.

In another implementation, the physical symptoms assessment data includes dizziness data.

In another implementation, the patient data includes safe functional motion data.

In another implementation, the safe functional motion data includes spinal compression forces.

In another implementation, the safe functional motion data includes balance and coordination.

In another implementation, upper and lower extremity flexibility and strength and trunk flexibility and strength are measured.

In another implementation, the output includes spinal curve reports.

In another implementation, the output includes strength reports.

In another implementation, the output includes flexibility reports.

In still another implementation, the patient data includes valued activities checklist data.

In another implementation, correlating the patient data and the osteoporosis data includes developing therapy recommendations and developing activity modifications.

In yet another implementation, the output includes therapy recommendations reports.

In another implementation, the output includes known therapy recommendations based on analysis of typical problem combinations.

In another implementation, the known therapy recommendations are based on a process that is based on safe functional motion data.

In another implementation, the output includes activity modification reports.

In another implementation, the activity modification reports are based on a process that is based on safe functional motion data.

In another implementation, the output includes activity risk reports.

In another implementation, the activity risk reports are generated from a process that generates data based on valued activities data and safe functional motion data.

In another implementation, the output includes graphical bone safety evaluation reports.

In another implementation, the output is generated by a process that uses safe functional motion data, physical symptom assessment data and bone mineral density data with the application of the disclosed formula for determining actual force and theoretical force.

In another implementation, the reports include a safety domain performance graph.

In another implementation, the reports include a spinal abnormalities graph.

In another implementation, the graph indicates the extent of spine curvature as measured by a plurality of curve points.

In another implementation, the reports include a activities-based fracture risk.

In another aspect, the invention features a bone safety evaluation method, including determining a patient's valued activities, physical symptoms data, bone mineral density, height and weight, determining the patient's safe functional motion by evaluating the patient's performance of a group of pre-determined tasks, using the physical symptoms data, safe functional motion, bone density data, height and weight to calculate a compressive strength of a region of interest of the patient and generating an activity risk, therapy recommendation and activity modification report based on patient's valued activities and compressive strength. The reports can further include a functional risk for fracture index.

In one implementation, the predetermined tasks are chosen from the group consisting of: pour; footwear; newspaper; reach-lift; sweep; washer; dryer; sit to floor; carry-climb; and night walk.

In another implementation, the compressive strength of a region of interest is calculated from a ratio of an actual force in the region of interest to a theoretical failure force in the region of interest.

In another implementation, the theoretical force is calculated by the following formula: $F=(16875 \text{ N/g/cm}^2)*(\text{Bone Mineral Density})-4875 \text{ N}$.

In another implementation, the ratio is optionally multiplied by a safety factor coefficient.

In another aspect, the invention features a bone safety evaluation method, including collecting physical symptoms assessment data, collecting safe functional motion data, collecting bone mineral density data, collecting patient demographic data and calculating a vertebral fracture risk based on the physical symptom assessment, safe functional motion, bone mineral density and demographic data.

In one implementation, the method further includes generating a bone safety evaluation report.

In another implementation, the method further includes collecting valued activities checklist data.

In another implementation, the method further includes analyzing patient performance of the valued activities checklist data.

In another implementation, the method further includes generating an activity risk report.

In another implementation, the method further includes performing an activity analysis based on a preselected task set.

In another implementation, the method further includes generating a therapy recommendation and activity modification report.

One advantage of the invention is that known osteoporosis data can be specifically applied to a patient to quantify risks associated with certain activities in which the patient engages.

Other objects, advantages and capabilities of the invention will become apparent from the following description taken in conjunction with the accompanying drawings showing the preferred embodiment of the invention.

BRIEF DESCRIPTION OF THE DRAWINGS

FIG. 5 illustrates an embodiment of a safe functional mobility scoring sheet;

FIG. 6 illustrates an embodiment of a therapy if-then document;

DETAILED DESCRIPTION

Figure 1:
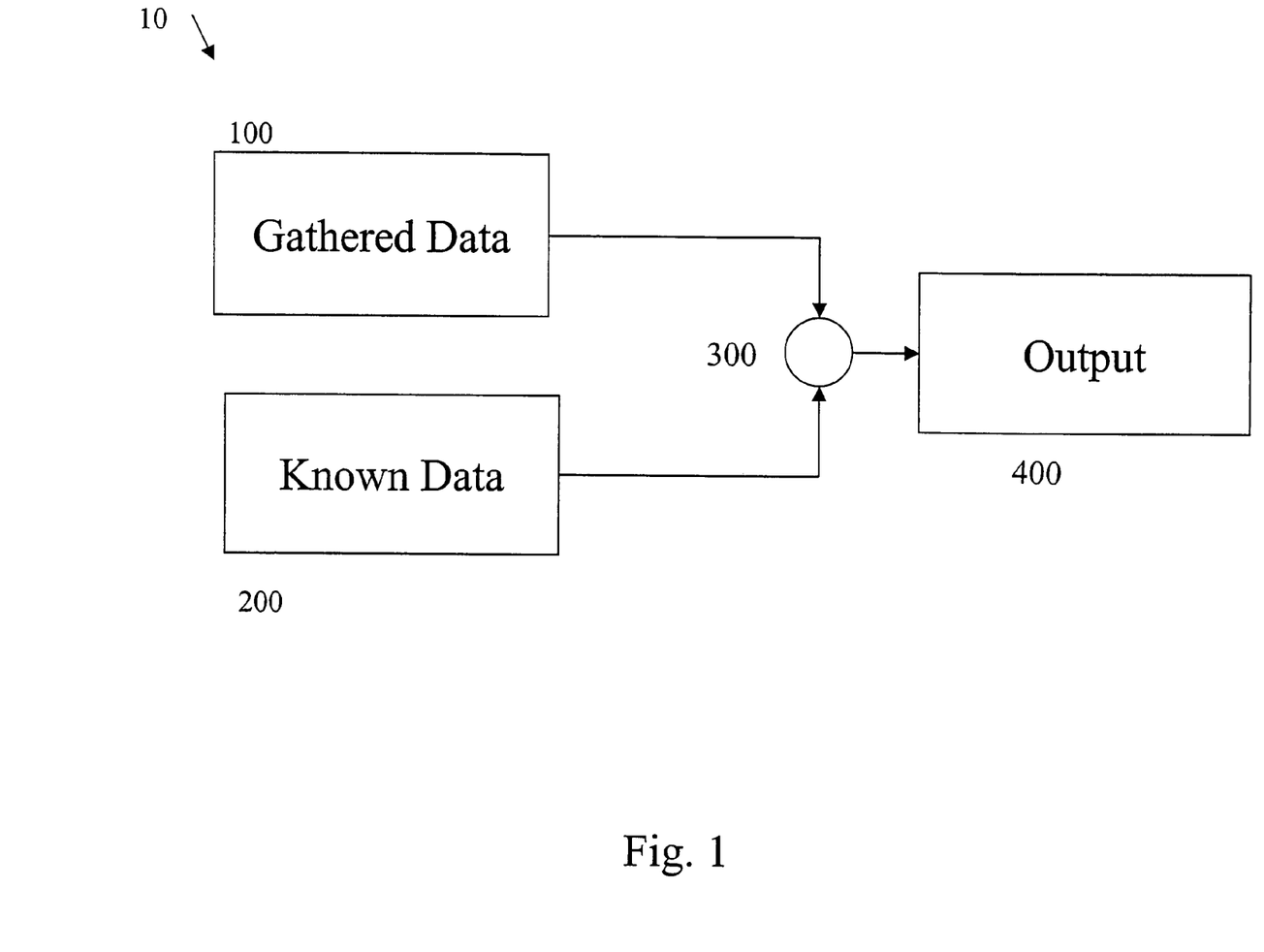
FIG. 1 illustrates an overall system level diagram of an osteoporosis management method.

Referring to the drawings wherein like reference numerals designate corresponding parts throughout the several figures, reference is made first to FIG. 1 that illustrates an overall system level diagram of a bone safety evaluation method 10, which can be specific to analyzing the risks associated with osteoporosis, including but not limited to functional fracture risk assessment, therapy needs determination and therapy progress measurement. In general, it is understood that the systems and methods described herein are performed by a trained practitioner including doctors, nurse practitioners, physician assistants, occupational therapists and the like. The term practitioner is used throughout and is understood to include all suitable professionals trained and educated to make the analyses discussed herein. In general, the method 10 and system implementing the method 10 includes collecting gathered data 100, typically related to the movement patterns and valued activities of a patient and known data 200 and entering the data 100, 200 into a process 300 that analyzes and assesses the data 100, 200 to generate output 400.

In a typical embodiment, the gathered data 100 includes data about the patient as discussed further below. In addition, the known data 200 includes data related to bone safety and fracture risk in general and related to osteoporosis. Known data, or throughput, typically includes data about compression forces as well as bone mineral density, although bone mineral density is also patient-specific as described further below. In general, known data can include an analysis of a set of pre-determined tasks and how a patient performs those tasks. By analyzing the set of tasks, a practitioner can evaluate the movement patterns specific to that patient. Movement patterns can include, twisting, bending, upper and lower extremity strength and trunk strength. These movement patterns can be used and applied to the valued activities of a patient and certain conclusions can be made about the valued activities based on how the patient performed the pre-determined tasks. A logic flow can be used to come to these conclusions. For example, if the practitioner determines that the patient engages in certain spinal compression forces when performing a task using bending, the practitioner can inform the patient that the patient is at increased risk of fracture in all the valued activities that use the similar bending movement pattern. A further detailed description of these types of analyses are discussed below.

The process 300 generally includes correlating the patient data and the osteoporosis data, which can include developing therapy recommendations and developing activity modifications. The process 300 can typically include both software generated calculations as well as evaluations, for example, based on question and answer, as performed by a practitioner. The method 10 further includes generating the output 400 relating to bone safety data specific to the patient, fracture risks and other osteoporosis risks to the patient based on the valued activities of the patient.

Figure 2:
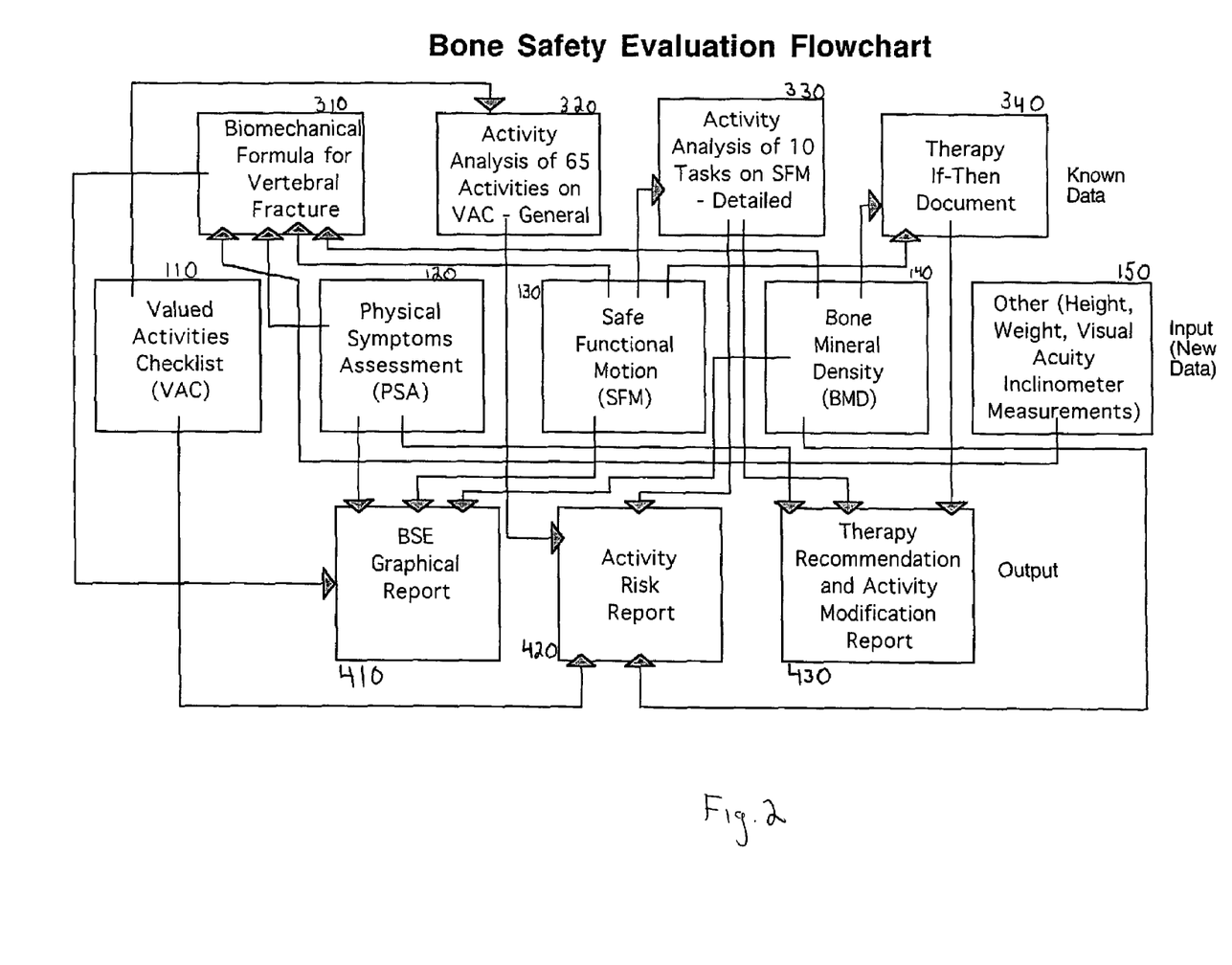
FIG. 2 illustrates a more detailed system level diagram as illustrated in FIG. 1.

FIG. 2 illustrates a more detailed system level diagram as illustrated in FIG. 1. In general, the method 10 includes input that can include a valued activities checklist 110, physical symptoms assessment 120, safe functional motion 130, bone mineral density 140 and demographic patient information 150, typically including height and weight. The method also includes throughput 300. The process 300 or throughput can typically include software processes such as a formula for vertebral fracture 310 based on the physical symptoms assessment 120, safe functional motion 130, bone mineral density 140 and the patient's demographic data 150. A detailed discussion of the vertebral fracture process 310 is found in the description below. The process 300 can further include an activity analysis 320 of the activities from the valued activities checklist 110, an activity analysis 330 of a pre-selected group of activities based on the safe functional motion 130 and a therapy if-then document 340 based both on the physical symptoms assessment 120 and the safe functional motion 130. The pre-selected group of activities is a specific set of activities that have been pre-analyzed for the compression exerted on the spine when the activity is performed, the movement patterns typically used to perform the activities, such as twisting and bending, and the upper and lower extremity and trunk strength typically used to perform them. Therefore, as discussed further in the description below, the pre-selected group of safe functional motion activities are useful for the practitioner to analyze a patient's movement patterns and make conclusions about risks, such as functional fracture risk, and recommendations for therapy and movement modifications, such as strength or flexibility training, or bending at the knees instead of at the waist when picking something from the floor.

Finally, the method 10 can also include the output including a bone safety evaluation report 410 that is generated from data from the vertebral fracture process 310 and the activity analysis 330, an activity risk report 420 generated from the vertebral fracture process 310 and the activity analysis 320 and a therapy recommendation and activity modification report 430 based on the data from the vertebral fracture process 310, the activity analysis 330 and the therapy if-then document 340.

Patient Data Input

As described above, the method 10 includes input that can include a valued activities checklist 110, physical symptoms assessment 120, safe functional motion 130, bone mineral density 140 and demographic patient information 150, typically including height and weight.

Figure 3A:
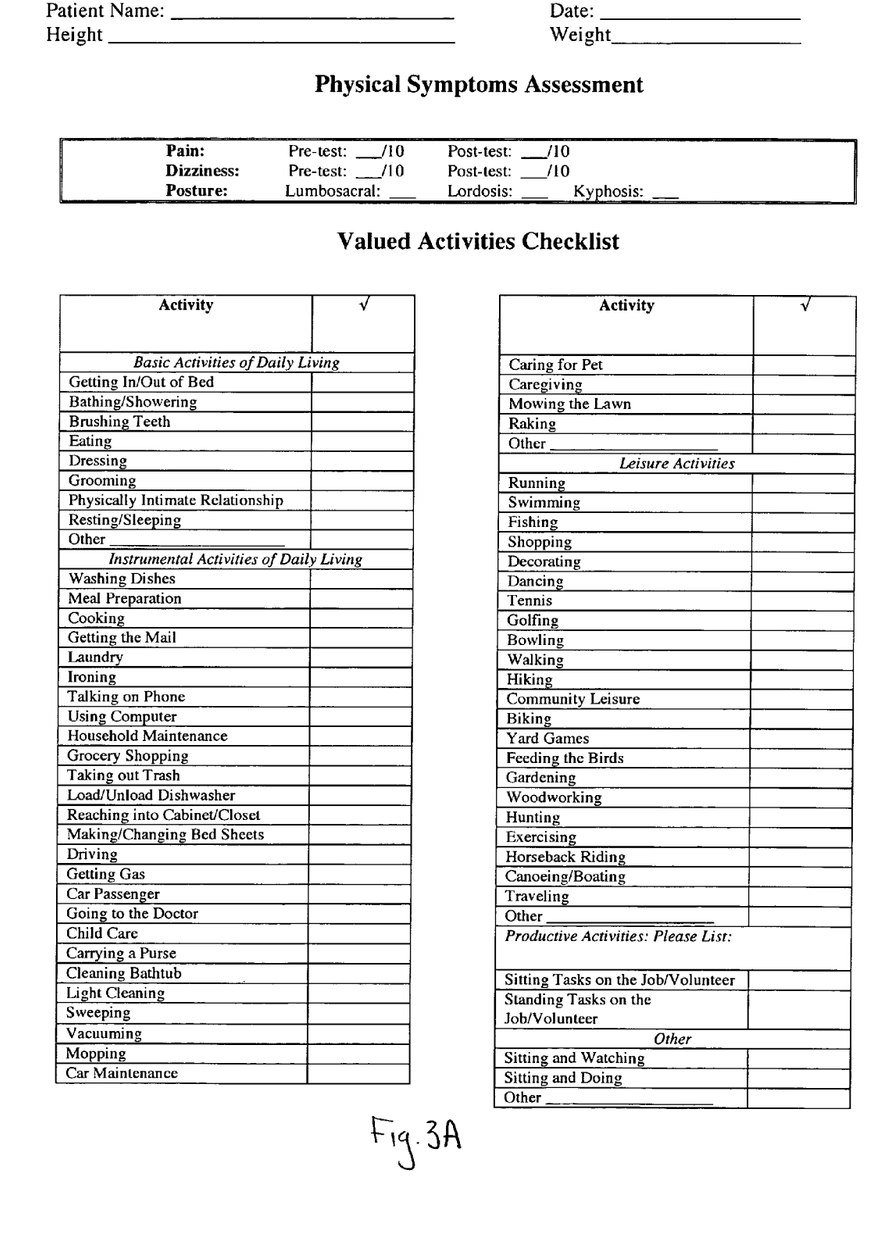
FIG. 3A illustrates an embodiment of a valued activities checklist.

The patient data typically also includes valued activities checklist 110 data. In general, the valued activities checklist 110 can be an all inclusive list or an open list subject to changes, additions and deletions. It is understood that the valued activities checklist 110 can include a limitless number of activities. In one embodiment, the valued activities checklist 110 can include but is not limited to basic activities of daily living such as getting in and out of bed, bathing/showering, brushing teeth, eating, dressing, grooming, physical intimacy, resting and sleeping. The valued activities checklist 110 can further include instrumental activities of daily living such as washing dishes, preparing meals, cooking, getting mail, laundry, ironing, talking on the phone, using a computer, maintaining the household, grocery shopping, taking out trash, loading and unloading a dishwasher, reaching into a cabinet or closet, making the bed and changing sheets, driving, getting gas, being a car passenger, going to the doctor, caring for a child, carrying a purse, cleaning a bathtub, light cleaning, sweeping, vacuuming, mopping, dusting, maintaining a car, caring for a pet, care giving, sitting and watching, sitting and doing, mowing the lawn and raking. The valued activities checklist 110 can further include leisure activities such as running, swimming, fishing, shopping, decorating, dancing, playing tennis, golfing, bowling, walking, hiking, community leisure, biking, playing yard games, feeding the birds, gardening, woodworking, hunting, exercising, horseback riding, canoeing/boating and traveling. The valued activities checklist 110 can further include productive activities such as sitting tasks on a job or volunteer position and standing tasks on a job or volunteer position. Typically, the patient can input the valued activities into the system implementing the method through data input such as a checklist or by choosing from a visual checklist such as images on a computer screen. For Example, FIG. 3A illustrates an embodiment of a valued activities checklist.

The patient data typically also includes physical symptoms assessment data 120. The physical symptoms assessment data can include several subtests such as a posture subtest and a pain and dizziness subtest. In a typical embodiment, for the posture subtest, a number of data points can be requested. In a typical implementation, three scores are used: a lumbosacral angle; L1/T12; and T1/C7. These three scores are typically obtained using an inclinometer at the three specific regions. These three regions and thus data points are used to determine a patient's spinal curvature. It is known that curvature can increase spinal compression forces, this increasing fracture risk. In particular, a pronounced T1/C7 score greatly increases fracture risk. Therefore, knowledge of the patient's curvature can further be used to know the fracture risk. As mentioned above, the physical symptoms assessment data includes pain and dizziness data derived from a pain and dizziness subtest. In general, the patient is asked to report the pain and dizziness as pain and dizziness scores before the test and the pain and dizziness as pain and dizziness scores after the test. The pain and dizziness are typically measured before and after the activities analysis 330 as discussed further below. In a typical embodiment an algometer is used to measure pain and dizziness, however, the patient can simply be asked to rate the pain and dizziness on a scale from 0-10, where 0 is no pain and 10 is excruciating pain.

The patient data can further include safe functional motion data 130. In general, the safe function motional data is a series of tests that helps determine certain risks associated with basic activities. The safe functional data can include balance and coordination. In general, a determination of balance and coordination is made by determining whether a patient experiences no loss of balance, unsteadiness or loss of balance during the evaluation. Typically, with no loss of balance, the patient is able to maintain balance using ankle strategies and needs no assistance to complete a given task. With unsteadiness, the individual uses the upper extremities to steady him or herself. In addition, the practitioner giving the evaluation might also give some assistance to maintain balance. The individual may also use step strategy or a wide base of support to maintain balance. The individual also may need to lean on an object to support the body weight and maintain balance. With loss of balance, the individual is only able to maintain balance with assistance from the practitioner.

The safe functional motion 130 data can also include spinal compression forces. Spinal compression forces generally include all the known forces that act on the spine during various activities. In order to make a proper risk assessment for a patient, the known forces on the spine must be correlated with the activities in which the patient normally engages. The goal is to determine a functional fracture risk index that can be correlated with certain activities to calculate a quantified risk associated with those activities. As such, the index helps to quantify the patient's vertebral fracture risk for various activities based on factors including the bone mineral density, height, weight and position during the activity. The spinal compression forces are discussed in more detail below with respect to the vertebral fracture process 310.

The safe functional motion 130 data can also include specific tasks including: pour; footwear; newspaper; reach-lift; sweep; washer; dryer; sit to floor; carry-climb; and night walk. These tasks are representative of a group of tasks that are useful in making movement pattern determinations. It is understood that some tasks may be removed or other tasks be added in other embodiment. The group of tasks, also known as safe functional motion tasks, is discussed further in the description below. In general, the tasks have been assembled for the purpose of efficiently gathering the most information of human motion based on six areas of concern, including upper and lower extremity/body strength and flexibility, trunk strength and flexibility, balance and coordination and spinal compression forces. It is therefore understood that the task list is exemplary and can be compiled from different exemplary tasks.

In general, as described further below, the observations of patient's movement patterns based on the ten tasks can be applied to the activities that the patient has checked on the valued activities checklist. If the patient is engaging in a safe functional motion activity in a way that uses spinal compression forces, the practitioner can make a conservative conclusion that the patient is probably using spinal compression in the activities on the valued activities checklist. In general, a patient with osteoporosis often must be advised that in an activity in which most people without osteoporosis engage, certain movement patterns are used that can cause no problems for the person without osteoporosis. However, those same movement patterns for a person with osteoporosis can cause risk such as fracture risk.

The patient data can further include bone mineral density (BMD) 140 that is typically acquired from various sources, including but not limited to dual energy x-ray absortiometry (DXA) and CT scans. The bone mineral density can be measured from a variety of locations along the spine, the hip or other areas of interest. In a typical embodiment for evaluating fracture risk associated with osteoporosis, the bone mineral density is measured in the L1-L4 region of the spine.

In general, the personalized demographic patient data 150 can include demographic data about the patient, such as the name and particular identification number assigned to the patient. In a typical embodiment, the data can be entered into the input device of the system when prompted.

Patient Data Throughput

As described above, the method 10 includes throughput including software processes such as a formula for vertebral fracture 310 based on the physical symptoms assessment 120, safe functional motion 130, bone mineral density 140 and the patient's demographic (such as height and weight) data 150, an activity analysis 320 of the activities from the valued activities checklist 110, an activity analysis 330 of a preselected group of activities based on the safe functional motion 130 and a therapy if-then document 340 based on the physical symptoms assessment 120, the safe functional motion 130 and bone mineral density 140.

The throughput 300 includes a vertebral fracture process 310. In vertebral fracture process 310, formula are used to determine (i) the actual forces that occur in a vertebral body during a particular task or groups of tasks and (ii) the theoretical force on a vertebral body based on the bone mineral density. Furthermore, calculation of the fracture risk, which is typically the ratio of the actual force to the failure force, is determined. A fracture risk greater than or equal to one indicates a high risk of vertebral fracture during the particular task. This fracture risk greater than or equal to one is a theoretical fracture threshold, where a conservative assumption of functional fracture occurs in theory. Therefore, a practitioner can warn the patient that a fracture is imminent. As discussed further below, a safety factor can be multiplied into this fracture risk ratio so that the number can be factored up to leave a safety range before the fracture threshold is actually reached. It has been determined that although no actual fracture has occurred at the threshold, micro-fracturing does occur at the threshold. Therefore, a full fracture may occur over time each time the patient engages in a movement that meets or exceeds the threshold. It is thus desirable to multiply the safety fracture to help prevent fill fracture and microfracture. In one embodiment, specific concern is given to the calculation of actual and theoretical forces and the fracture risk of L3 in the lumbar spinal region as the region of interest.

Figure 4:
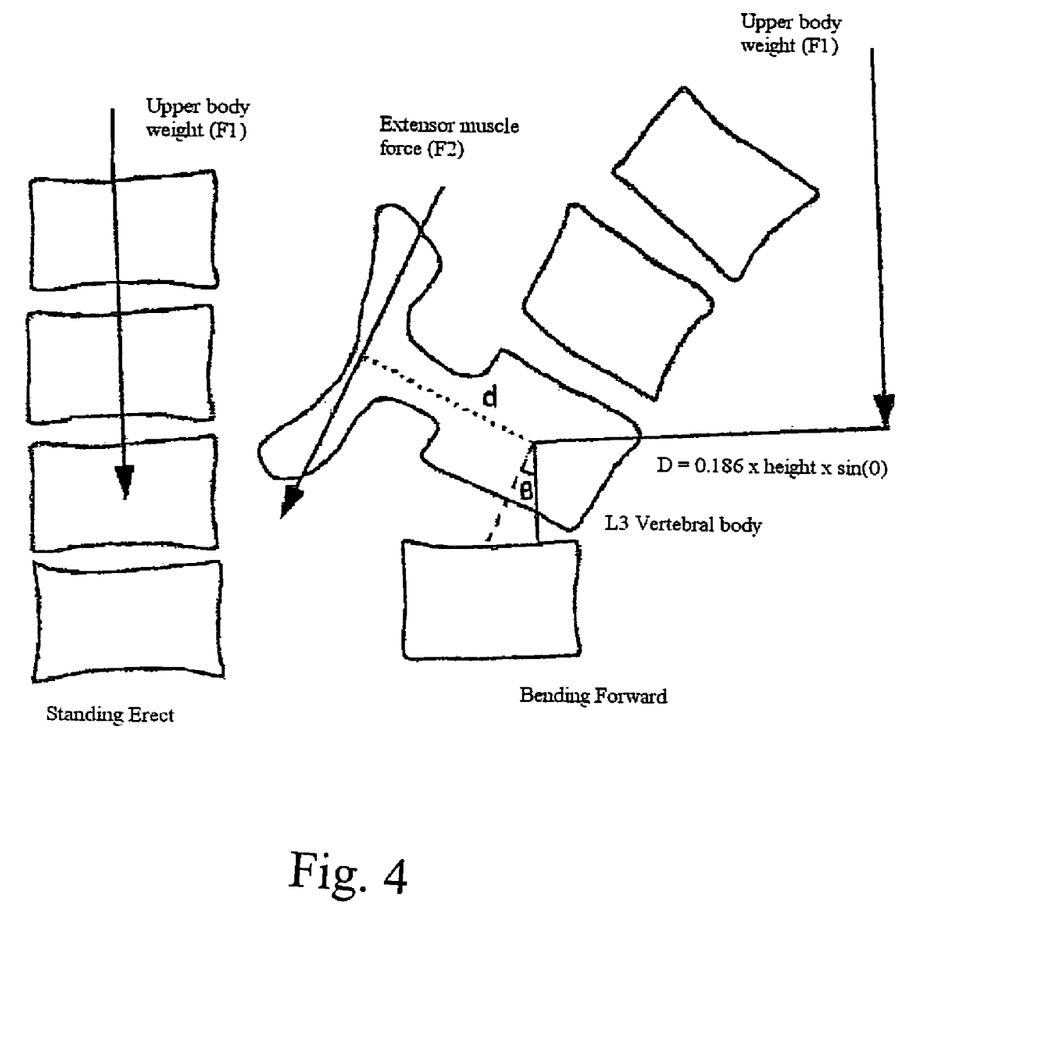
FIG. 4 illustrates a graphical representation of the forces on a vertebral body.

Typically, the loads and therefore forces on a vertebral body are determined using body weight, height and the moment arm of the muscle attached to the vertebral body. The force can be calculated by:

$$F=(0.455)(Weight)[Cos(\theta)+(0.186)(Height)(Sin(\theta))/d]$$

where weight is the patient's body weight, height is the person's height, theta is the angle of forward bending, and d is the extensor muscle moment arm. FIG. 4 illustrates a graphical representation of the forces on L3 based on the above formula. The values for the muscle moment arm can be obtained from various sources such as lateral dual energy x-ray absortiometry (DXA) scans. The values for d can be calculated from patient groups based on common data to the patients of concern. In one implementation, d=2.9 cm (d=1.14173 inch) as chosen for a patient group of elderly women and women with vertebral fractures. It is understood that other criteria and patient groups can be used in other implementations.

Theoretical failure forces can be determined based on strong correlations between bone mineral density measured with DXA and the compressive strength of lumbar vertebral bodies. From the strong correlation a slope and equation of the linear trendline can be calculated. The following equation describes the relationship between lateral bone mineral density ($g/cm^2$) and the maximum compressive strength ($F_{max}$) of a vertebral body:

$$F_{max}=(16875\ N/g/cm^2)*(BMD)-4875\ N(\text{load in Newtons})$$

$$F_{max}=(3793.65\ lb/g/cm^2)*(BMD)-1095.94\ lb(\text{load in pounds})$$

The above $F_{max}$ were determined for L3. However, in addition, there is a strong relation between bone mineral properties measured with lumbar DXA and the compressive strength of the second lumbar body (L2) as well as the eleventh thoracic vertebral body (T11). This relation indicates that lumbar bone mineral properties can be useful indicators of fracture risk for both lumbar and thoracic fractures.

The fracture risk can be calculated as the ratio of the actual force during activities to the theoretical failure force ($F_{max}$):

$$FR=\text{Actual Force/Failure Force}$$

A value of FR> or =1 indicates that the patient is at high risk for vertebral fracture during that particular activity. In one embodiment, several assumptions can be factored into the model as a safety factor SF.

$$FR=\text{Actual Force}*SF/\text{Failure Force}$$

In this embodiment, the assumptions can include: a rigid body model that does not account for the individual joints of the spine; the exclusion of kyphosis, lordosis or individual variations in the trunk shape and the like of the patient; the exclusion of twisting and rotation and the associated muscle forces; extensor force is the only force counteracting the body weight, excluding facet ligaments and joint with shorter moment arms; and that all flexion occurs at L3, which actually overestimates the effects of body weight as a more conservative assumption. It is understood that the assumption may or may not be included in the model in other embodiments. It is further understood that the above-discussed formulas can change depending on new data, discoveries, assumptions and the like.

The process 300 can further include an activity analysis 320 of activities from the valued activities checklist 110, an activity analysis 330 of a preselected group of activities based on the safe functional motion 130 and a therapy if-then document 340 based both on the physical symptoms assessment 120 and the safe functional motion 130. In general, the activity analysis 330 of the preselected group of tasks is an assessment made independent and prior to any interaction with a patient. For example, the preselected group can include 10 tasks including pour, footwear, newspaper, reach-lift, sweep, washer, dryer, sit to floor, carry-climb, and night walk. These ten tasks are analyzed based on whether or not they include certain movements such as bending, twisting, strength, flexibility and balance shift. Therefore, a practitioner has a priori knowledge that certain tasks involve certain movements. Then when the practitioner actually evaluates a patient and has the patient perform the tasks, the practitioner can observe how a patient actually performs the tasks, and then make recommendations based on these observations. The tasks are discussed further in the description below. Similarly, the patient can be given a large list of activities either in list form or graphical form and ask the patient if she performs any of these tasks, which can then become the valued activities checklist 110. The activities analysis 320 on these tasks can then be performed and a determination whether or not certain movements such as bending, twisting and balance shift are used in those tasks.

In general, during the testing of the patient to determine the functional fracture risk, the patient can engage in several activities. Depending how the patient engages in the activities helps to determine the potential compression on the spine. For example, the patient can be asked to engage in certain activities that could involve bending and twisting of the spine. As such, compression forces can be determined depending on whether the patient squats or kneels to complete a task or uses adapted method to complete the task, such as using a reacher, sock aide, asks for assistance, golfer's reach, using a stool, a long handled dust pan or verbalizes safe method of completing a task. Furthermore, the compression forces can be determined depending on whether or not the patient bends at the waist or upper back (engages in spinal flexion at the lumbar or thoracic regions) at any time during the task, or whether or not the individual twists his spine or avoids spinal twisting.

In a typical implementation, the practitioner can use a variety of tasks to help determine the compression forces. As described above, the tasks are pre-determined and pre-analyzed for movement patterns. This predetermination and pre-analysis can then be applied to how the patient actually performs that tasks. It is understood that any suitable task group can be chosen, however, in one embodiment, the predetermined tasks are pour, footwear, newspaper, reach-lift, sweep, washer, dryer, sit to floor, carry-climb and night walk. In general, the patient can wear a safety belt throughout the tasks. Each task is now discussed separately.

The practitioner can ask the patient to engage in the pour task. Observations that can help determine the spinal forces include whether or not the patient carries the container close to herself and uses her trunk to assist in carrying the container, or rather carries the container away from her trunk and uses only arms and hands to carry the container. The patient can be asked to empty a full container into a cup at intervals and a determination can be made on how the patient performs this task. The practitioner can give time to the patient to feel the differences in each way the patient performs the task. In one implementation, if the patient engages in any type of flexion movement, the practitioner can ask the patient to modify the movement without using flexion and then ask if the patient feels the difference.

The patient can also be asked to engage in the footwear task. The patient is asked to remove both shoes and socks and put them back on. The practitioner can observe how the patient carries out this task and whether or not the way the patient is performing the task is the typical way the patient performs the task daily. In one implementation, if the patient does not use the ankle to knee approach, the practitioner can ask the patient if he or she can place the ankle on the opposite knee.

The patient can also engage in the newspaper task. In this task the patient is asked to lift a newspaper from the floor. The newspaper is typically placed in front of the patient. The practitioner asks if the way that the patient picks up the newspaper is the way the patient always engages in the activity. In one implementation, if the patient bends to pick up the newspaper, the practitioner can recommend that the patient uses squatting or kneeling to pick up the newspaper.

The patient can also engage in the reach-lift task. The patient is asked to place a container on the highest shelf that the patient can reach. The patient picks up the container, places it on the highest shelf, then removes it. The practitioner can observe whether or not the patient reaches with both feet flat on the floor or uses a reacher to retrieve an item, or whether or not the patient comes up on one or both tip toes during the reach. The practitioner can also observe specific details such as whether or not there is a greater than of less than or equal to a ninety degree range of motion when the patient places on object on a high surface. Typically, the practitioner is observing whether or not the patient can attain a ninety degree or greater shoulder flexion.

The practitioner can also ask the patient to engage in the sweep task. In one implementation, the practitioner spreads a volume of substance such as aquarium rocks or kitty litter in a 4'×3' (or other dimension) rectangle on the floor. The patient can be given a broom and dustpan and is asked to sweep the substance into the dustpan and set the dustpan on a counter. If the patient sweeps using spinal flexion, the practitioner can place the dustpan back on the floor and ask the patient if he or she can squat or kneel to pick up the dustpan.

The patient can also engage in the washer task. In one implementation, the practitioner can place towels and weights in the washer. From the front of the washer, the patient opens the washer door, transfers all the towels and weights to the dryer and closes the dryer door.

The patient can also engage in the dryer task. In one implementation, the patient starts in front of the dryer, opens the dryer door, transfers the contents of the dryer to a laundry basket. The patient then moves the basket anywhere the patient wishes. The patient then puts the basket on top of the dryer and closes the dryer door. The practitioner can then place the basket behind the patient and ask the patient to pick up the basket. IF the patient cannot pick up the basket, the practitioner can remove some of the towels and asked again to pick up the basket. In general, if the patient uses spinal flexion to remove towels from the dryer and pick up the basket, then the basket can be replaced on the floor and the patient can be asked if he or she can squat or kneel to pick up the basket.

The patient can also engage in the sit to floor task. In one implementation, the patient is asked to sit down to the floor, stretch his or her legs out in front and then come back to the standing position. A chair can be placed next to the patient for help is needed. In addition, the practitioner can hold the patient's belt to prevent the patient from dropping to the floor or to assist in lifting the patient.

The patient can also engage in the carry-climb task. In one implementation, the patient carries groceries from the kitchen, out of the doorway, over to stairs, up the stairs and down the stairs. The patient can use a railing if needed. However, it is desirable for the patient to refrain from using the railing. The patient then walks back to the kitchen and looks from one wall to another ten times as fast as possible. This head movement helps to simulate looking around such as in a parking lot. This movement is used to determine whether or not the patient becomes unsteady. The patient then walks back to the kitchen and places the bags on a shelf above the sink. The patient is asked to place as much weight as possible in the bags, knowing how far he or she has to travel. The patient is asked to carry the bags in any way. In general, the practitioner adjusts the weight and observes how the patient carries the bags, that is evenly or all in one hand and the like.

The patient can also engage in the night walk task. In one implementation, the patient stands up from a sofa, walks over a rug and steps up on top of a foam obstacle under the rug two times. The lights are on for the first trial, and off for the second. The patient also wears sunglasses on the second trial to further dim the light. This task simulates a night walk.

In general, the practitioner can determine pain and dizziness before and after the tests. In addition, during the performance of these task, the practitioner can take pain and dizziness readings as described above. Furthermore, the practitioner can take certain spinal measurements at this time. The practitioner can measure three spinal angles such as lumbosacral, T12-L1 interspace and C7-T1 interspace.

With the vertebral fracture analysis that provides the risk index based on spinal compression forces associated with a particular patient, and a knowledge of how a patient performs preselected tasks and valued activities tasks, therapy recommendations are risk reports can be provided to the patient. For example, by knowing the particular fracture risk and knowing that a patient bends during a particular known task, such as reaching, in which the patient should normally not be bending, that patient can be provided a risk analysis that she is at an increases fracture risk if she continues to bend when reaching and can be advised to modify her reaching to exclude bending. An additional example is if the same patient is at fracture risk for any twisting motion, she can be advised that if any of her valued activities include twisting, then she is at increased risk of fracture if she engages in those twisting activities. A suitable score can be associated with how the patient performs the tasks. In general, a score is associated with the balance and coordination with each task and a score is associated with the spinal compression present when the patient performs a particular task. FIG. 5 illustrates an embodiment of a safe functional mobility scoring sheet based on the tasks. In general, the score sheet is used by the practitioner to base relative scores based on how the patient performs the task. The resulting scores help the practitioner to make conclusions about the functional fracture risk and other risks, and therefore further help the practitioner to make therapy recommendations and activity modifications. It is understood that these examples are not exhaustive of the type of recommendations and risks that can be reported to a patient but are simply illustrative examples of the recommendations and risks that can be generated from the method and system.

The process 300 can further include the therapy if-then document 340 based both on the physical symptoms assessment 120 and the safe functional motion 130. The therapy if-then document 340 is a logic flow that helps the practitioner to develop the therapy recommendations and activity modifications as described further below with respect to the output 400.

In general, the if-then document 340 is a series of logic questions that help to make a final determination of therapy recommendations and activity modifications based further in view of the data gathered above. FIG. 6 illustrates an embodiment of a therapy if-then document 340. The if-then statements in FIG. 4 are only illustrative of the logic questions that can be used. It is understood that many other if-then statements are possible to aid in the evaluation and determination of therapy recommendations and activity modifications.

Patient Data Output

As described above, the method 10 can also include the output including a bone safety evaluation report 410 that is generated from data from the bone mineral density data 140, the demographic data 150, the vertebral fracture process 310 and the activity analysis 330, an activity risk report 420 generated from the vertebral fracture process 310 and the activity analysis 320 and a therapy recommendation and activity modification report 430 based on the data from the vertebral fracture process 310, the activity analysis 330 and the therapy if-then document 340.

Figure 7:
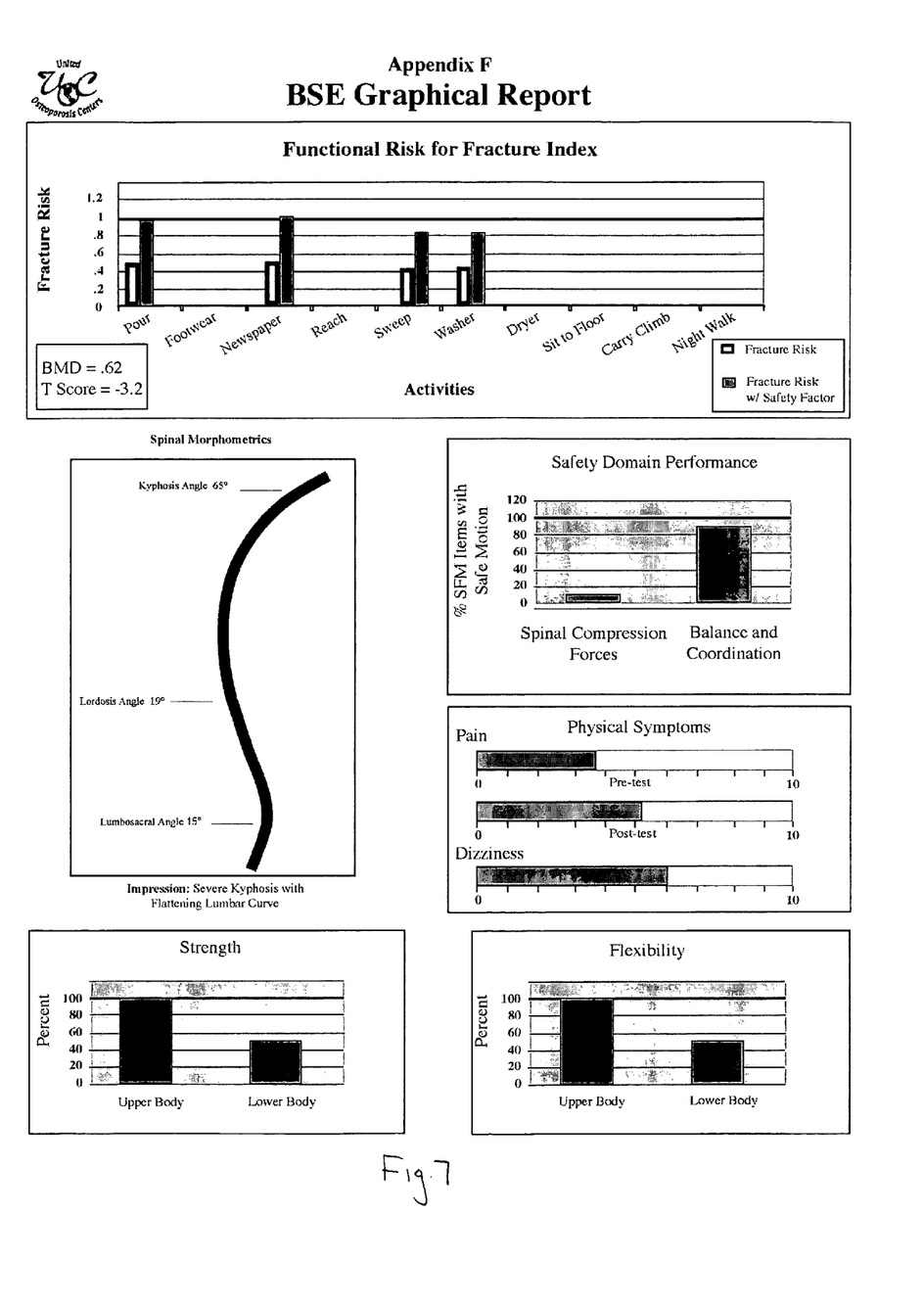
FIG. 7 illustrates an embodiment of a graphical bone safety evaluation report, including functional fracture risk, strength and flexibility, safe functional motion, spinal curve, pain and dizziness.

In a typical embodiment, the bone safety evaluation report 410 is a graphical report that illustrates important information specific to the patient including but not limited to activity-based fracture index, spinal morphemetrics, safety domain performance, physical symptoms, strength and flexibility. The graph helps to illustrate the compression forces on the spine based on the process 310 and the risk associated with particular activities from the activities analysis 330. The fracture risk typically differs from activity to activity. FIG. 7 illustrates an embodiment of a bone safety evaluation report. FIG. 7 includes an embodiment of a graphical bone safety evaluation report, including functional fracture risk, strength and flexibility, safe functional motion, spinal curve, pain and dizziness.

The safety domain performance portion indicates the percentage of items in which the patient engaged in safe functional motion during the activities analysis. The number is typically calculated using the scores obtained as discussed above. The spinal morphemetrics portion indicates the extent of curvature as measured by the three points as discussed above. The flexibility portion indicated whether the patient has some decreased range of motion in either the upper or lower extremities. The activity based fracture risk portion indicated the risk of vertebral fracture for each of the activities based on the patient's movements, the bone mineral density and the actual force to failure force ratio multiplied with and without the safety factor. The visual representation of the patient's response to pain and dizziness is also illustrated.

Figure 8:
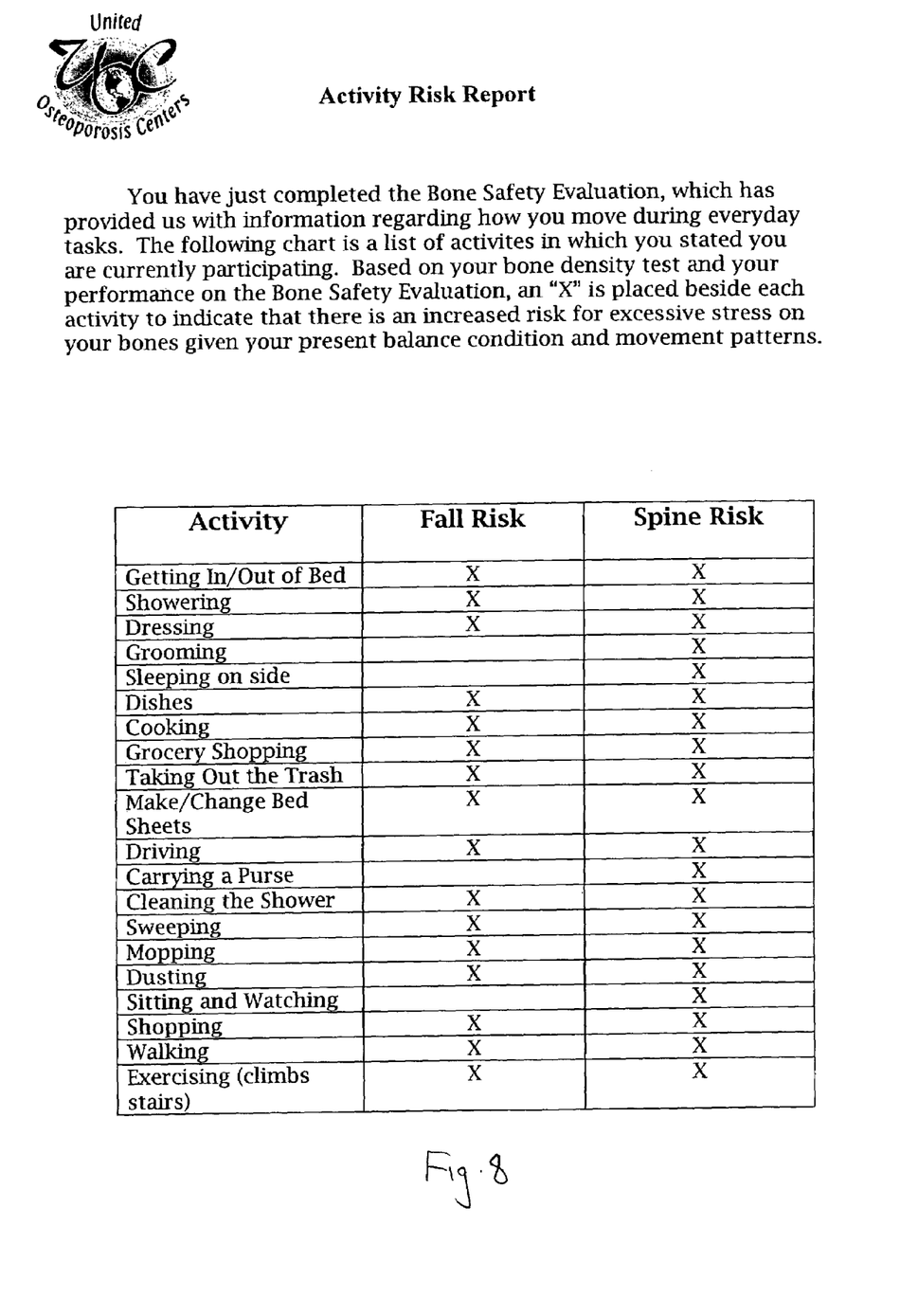
FIG. 8 illustrates an embodiment of an activity risk report.

The output 400 can further include an activity risk report 420 generated from the vertebral fracture process 310 and the activity analysis 320. The activity risk report 420 helps to further characterize the fracture risks that the patient experiences with the day to day valued activities that the patient has previously identified. FIG. 8 illustrates an embodiment of an activity risk report 420. Typically, an X in one of the columns indicates that there is a risk of fall or fracture associated with the particular activity. In a typical implementation, if a patient has a score of less than 100% on the balance and coordination sub-domain or spinal compression sub-domain, then the column for the corresponding domain includes the X indicating a fracture risk.

Figure 9:
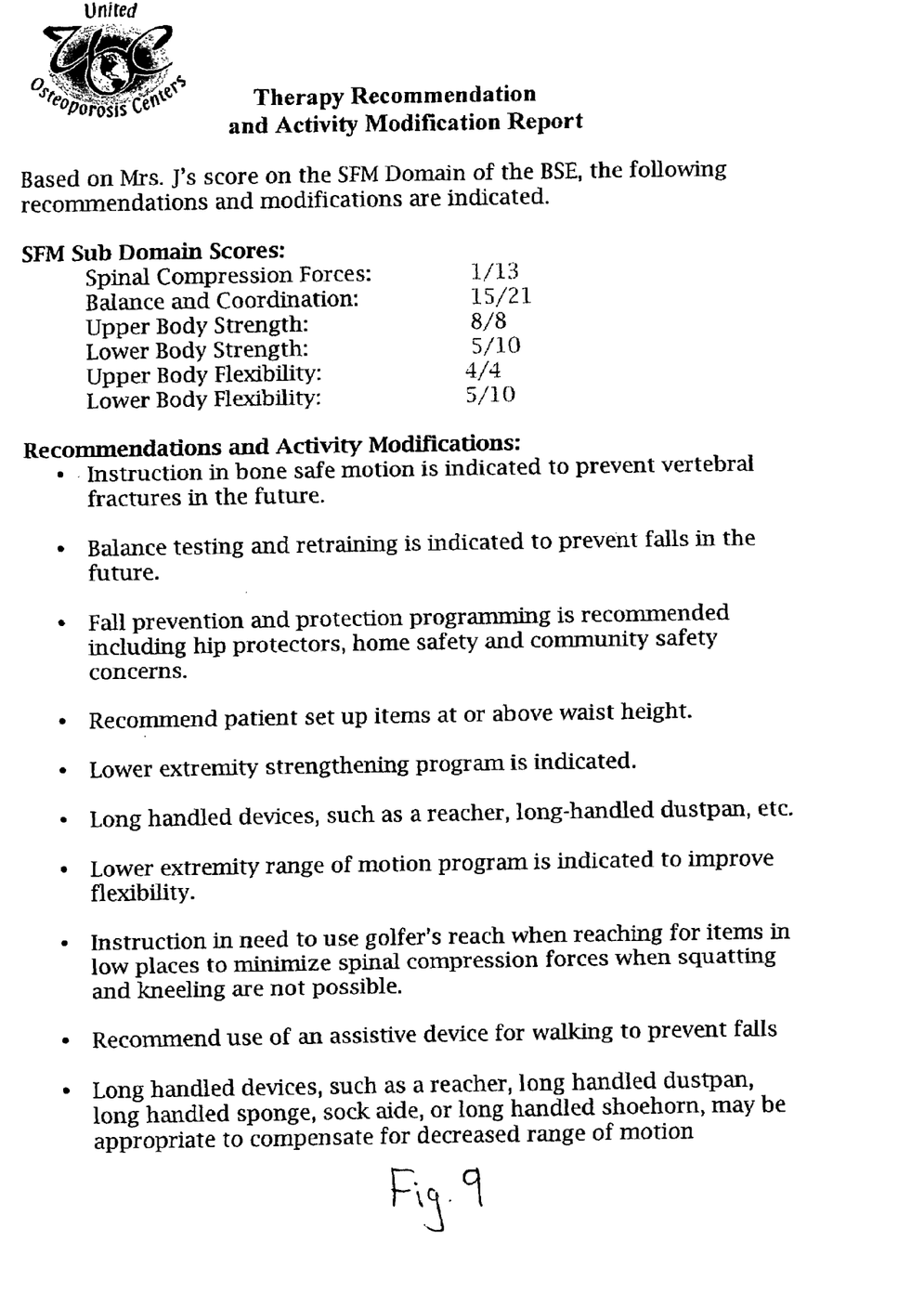
FIG. 9 illustrates an embodiment of a therapy recommendation and activity modification report.

The output 400 can further include a therapy recommendation and activity modification report 430 based on the data from the vertebral fracture process 310, the activity analysis 330 and the therapy if-then document 340. The therapy recommendation and activity modification report 430 can instruct a patient not only on therapy recommendations that can help the patient reduce the fracture risk, but also recommendations on how to change how the patient performs activities to further reduce fracture risk. For example, if the patient is bending while reaching as used in the example above, which is a known way to increase spinal compressions and thus fracture risk, the report 430 can recommend that the patient perform the reaching activity by excluding bending. FIG. 9 illustrates an embodiment of a therapy recommendation and activity modification report 430. In general the report lists safety and physical limitations. The practitioner can use the report to guide interventions during treatment so that the patient receives the most accurate and personalized treatment.

EXAMPLE

Mrs. J arrives for an appointment with a physician, has a bone density test, completes a clinical risk assessment screening form and is diagnosed (or has been diagnosed) with osteoporosis. Mrs. J has a T-score of −3.3 at L1-4 and −2.5 at both hips. She is given thorough medical care and is referred to engage in the methods as discussed herein.

Mrs. J arrives for the appointment to receive analysis based on the methods with the practitioner who begins to gather lifestyle information about the patient based on the valued activities checklist. Using physical symptoms assessment as described above, the practitioner assesses her spinal curves using an inclinometer, has Mrs. J rate the pain before the treatment on a visual analog scale and has her rate her dizziness on a visual analog scale as well.

The practitioner then explains to Mrs. J that she will be asked to perform ten typical tasks/motions of daily life and she will be rated in safety, balance, strength and flexibility (upper, lower and trunk). The practitioner then asks Mrs. J to engage in these tasks as described above. Mrs. J is then rated on the safe functional domain score sheet as shown in FIG. 5. Once the score sheet is completed, the document is transformed into the personalized performance of Mrs. J. Following the performance of the tasks, she is asked to rate her pain and dizziness once again on the visual analog scale.

At this point, the processing of all the information begins. Referring again to FIG. 1, the above described analysis is the acquisition of the known and gathered data. The data is now processed at the juncture 300. First, the safe functional motion and physical symptoms assessment reports are combined with Mrs. J's bone mineral density score and the biomechanical formula is used to develop the bone safety evaluation report (see FIG. 7) as part of the output 400.

Mrs. J is then given the activity risk report (see FIG. 8) that summarizes her report of activities relative to her safe functional domain scores on balance and coordination, spinal compression forces and strength and flexibility. A visit can be scheduled to specifically address her risk areas.

The practitioner then uses the therapy recommendation and activity modification report (see FIG. 9). This report is based on the activity analysis of the typical tasks of everyday life (e.g., the ten tasks) and combined with traditional recommendations relative to strength, flexibility, engagement in spinal compression forces and risk for fall to provide thorough care to Mrs. J that is specific to her needs and abilities.

The software techniques and methods discussed above can be implemented in digital electronic circuitry, or in computer hardware, firmware (as discussed), software, or in combinations of them. Apparatus may be implemented in a computer program product tangibly embodied in a machine-readable storage device for execution by a programmable processor; and methods may be performed by a programmable processor executing a program of instructions to perform functions by operating on input data and generating output. Further embodiments may advantageously be implemented in one or more computer programs that are executable on a programmable system including at least one programmable processor coupled to receive data and instructions from, and transmit data and instructions, to a data storage system, at least one input device, and at least one output device. Each computer program may be implemented in machine language or assembly language which can be assembled or translated, or a high level procedural or object-oriented programming language, which can be complied or interpreted. Suitable processors include, by way of example, both general and special purpose microprocessors. Generally, a processor receives instructions and data from read-only memory and or RAM. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing may be supplemented by, or incorporated in, specially designed application specific integrated circuits (ASICs).

The foregoing is considered as illustrative only of the principles of the invention. Further, various modifications may be made of the invention without departing from the scope thereof and it is desired, therefore, that only such limitations shall be placed thereon as are imposed by the prior art and which are set forth in the appended claims.

What is claimed is:

1. A bone safety evaluation method, said method comprising:
    determining a patient's activities comprising assembling a list of one or more activities performed by the patient, physical symptoms data, bone mineral density, height and weight;
    determining the patient's safe functional motion by evaluating the patient's performance of a group of pre-determined tasks;
    inputting the patient's physical symptoms data, the patient's bone mineral density, and the patient's height and weight into an input device of a computer system;
    utilizing computer software on the computer system to calculate a fracture risk of a region of interest of the patient for one or more task within said group of pre-determined tasks, wherein the fracture risk of the region of interest is calculated from a ratio of an actual force in the region of interest to a theoretical failure force in the region of interest, and the fracture risk is utilized to form a functional risk for fracture index as a component of the one or more computer generated feedback reports, the actual force being calculated by the following formula:

$F=(0.455)(\text{Weight})[\text{Cos}(\theta)+(0.186)(\text{Height})(\text{Sin}(\theta))/d]$, and the theoretical failure force being calculated by the following formula:

$F=(16875 \text{ N/g/cm}^2)*(\text{Bone Mineral Density})-4875 \text{ N}$;

wherein:
        Weight represents the patient's weight;
        Height represents the patient's height;
        θ represents an angle of forward bending,
        d represents an exterior muscle moment arm, and
        Bone Mineral Density represents the patient's bone mineral density; and
    transforming data comprising the patient's safe functional motion alone or in combination with one or more of (i) the patient's activities, (ii) the patient's physical symptoms data, (iii) the patient's bone mineral density, height and weight, and (iv) the calculated fracture risk into one or more computer generated feedback reports via the computer software.

2. The method as claimed in claim 1, wherein the predetermined tasks are chosen from the group consisting of: a pour task; a footwear task; a newspaper task; a reach-lift task; a sweep task; a washer task; a dryer task; a sit to floor task; a carry-climb task; a night walk task; and any combination thereof.

3. The method as claimed in claim 1, wherein the ratio is optionally multiplied by a safety factor coefficient.

4. The method as claimed in claim 1, wherein the patient's physical symptoms data comprises spine curvature data.

5. The method as claimed in claim 4, wherein the patient's spine curvature data comprises a lumbosacral angle, a L1/T12 score, and a T1/C7 score.

6. The method as claimed in claim 1, wherein the region of interest is the patient's L3 lumbar region.

7. The method of claim 1, wherein the one or more computer generated feedback reports comprises a computer generated bone safety evaluation report comprising one or more graphically displayed report features generated from the calculated compressive strength in combination with the patient's physical symptoms data, the patient's safe functional motion data, and the patient's bone density data.

8. The method of claim 7, wherein the computer generated bone safety evaluation report comprises a graphical report comprising report features including a computer generated spinal curve graph, a computer generated strength graph, a computer generated flexibility graph, and a computer generated activity risk graph.

9. The method of claim 8, wherein the computer generated activity risk graph is based on computerized assessment of (i) the patient's activities data and (ii) the patient's safe functional motion data.

10. The method as claimed in claim 1, wherein the one or more computer generated feedback reports comprises a computer generated activity risk report based on assessment of the patient's performance of the patient's activities on the list of one or more activities periodically performed by the patient.

11. The method as claimed in claim 1, wherein the one or more computer generated feedback reports comprises a computer generated therapy recommendation and computer generated activity modification report based on assessment of the patient's safe functional motion.

12. A bone safety evaluation method, said method comprising:
    collecting physical symptoms assessment data of a patient, said physical symptoms assessment data comprising posture data, pain data and dizziness data;
    collecting safe functional motion data of the patient, said safe functional motion data comprising an evaluation of the patient's performance of a group of pre-determined tasks;
    collecting bone mineral density data of the patient;
    collecting demographic data of the patient;

inputting the physical symptoms assessment data, the safe functional motion data, the bone mineral density data, and the demographic data into an input device of a computer system;

utilizing computer software on the computer system to calculate a vertebral fracture risk for a particular task with said group of pre-determined tasks based on inputted patient data comprising the safe functional motion data, and the bone mineral density data.

13. The method as claimed in claim 12, further comprising utilizing the computer software on the computer system to generate a bone safety evaluation report comprising one or more report features generated from one or more pieces of inputted or computer-calculated data selected from the calculated data vertebral fracture risk of the patient, the physical symptom assessment data of the patient, the safe functional motion data of the patient, the bone mineral density data of the patient, and the demographic data of the patient.

14. The method as claimed in claim 12, further comprising:

collecting activities data of the patient, wherein the activities data comprises a list of one or more activities performed by the patient; and inputting the activities data of the patient into the input device.

15. The method as claimed in claim 14, further comprising utilizing the computer software to generate a computer generated activity risk report from inputted data comprising the patient's performance and movement during (i) one or more safe functional movement tasks and (ii) one or more activities on the list of one or more activities performed by the patient.

16. The method as claimed in claim 15, wherein one or more tasks within the group of pre-determined tasks are selected from the group consisting of: a pour task; a footwear task; a newspaper task; a reach-lift task; a sweep task; a washer task; a dryer task; a sit to floor task; a carry-climb task; a night walk task; and any combination thereof.

17. The method as claimed in claim 14, wherein the step of collecting activities data of the patient comprises compiling the list of one or more activities performed by the patient.

18. The method as claimed in claim 12, wherein the step of collecting safe functional motion data of the patient comprises analyzing the patient's performance and movement while performing one or more tasks within said group of pre-determined tasks.

19. The method as claimed in claim 12, further comprising utilizing the computer software on the computer system to generate a computer generated therapy recommendation and computer generated activity modification report.

20. The method as claimed in claim 12, wherein the patient's physical symptoms assessment data comprises spine curvature data.

21. The method as claimed in claim 20, wherein the patient's spine curvature data comprises a lumbosacral angle, a L1/T12 score, and a T1/C7 score.

22. The method as claimed in claim 12, wherein the vertebral fracture risk for a particular task is calculated as a ratio of an actual force in a region of interest to a theoretical failure force in the region of interest while performing the particular task, the actual force being calculated by the following formula:

$$F = (0.455)(\text{Weight})[\text{Cos}(\theta) + (0.186)(\text{Height})(\text{Sin}(\theta))/d],$$

and the theoretical failure force being calculated by the following formula:

$$F = (16875 \text{ N/g/cm}^2) * (\text{Bone Mineral Density}) - 4875 \text{ N};$$

wherein:

Weight represents the patient's weight;

Height represents the patient's height;

$\theta$ represents an angle of forward bending, d represents an exterior muscle moment arm, and Bone Mineral Density represents the patient's bone mineral density.

23. The method as claimed in claim 22, wherein the vertebral fracture risk for one or more tasks is utilized to form a functional risk for fracture index as a component of one or more computer generated feedback reports generated from the inputted patient data.

24. A bone safety evaluation method, said method comprising:

collecting safe functional motion assessment data alone or in combination with activities assessment data of the patient, said safe functional motion data comprising an evaluation of the patient's performance of a group of pre-determined tasks, and said activities assessment data comprising compiling a list of one or more activities periodically performed by the patient, wherein said step of collecting safe functional motion data of the patient comprises determining the fracture risk for one or more task while performing the one or more tasks from the group of pre-determined tasks, wherein the fracture risk for a particular task is calculated as a ratio of an actual force in a region of interest to a theoretical failure force in the region of interest while performing the particular task, the actual force being calculated by the following formula:

$$F = (0.455)(\text{Weight})[\text{Cos}(\theta) + (0.186)(\text{Height})(\text{Sin}(\theta))/d],$$

and the theoretical failure force being calculated by the following formula:

$$F = (16875 \text{ N/g/cm}^2) * (\text{Bone Mineral Density}) - 4875 \text{ N};$$

wherein:

Weight represents the patient's weight;

Height represents the patient's height;

$\theta$ represents an angle of forward bending, d represents an exterior muscle moment arm, and Bone Mineral Density represents the patient's bone mineral density;

collecting bone mineral density assessment data, height and weight of the patient; and inputting (i) the patient's safe functional motion assessment data alone or in combination with the activities assessment data of the patient, (ii) the patient's bone density assessment data, and (iv) the patient's height and weight into an input device of a computer system;

utilizing computer software on the computer system to calculate a fracture risk of a region of interest of the patient for one or more task within said group of pre-determined tasks; and transforming inputted data comprising (i) the patient's safe functional motion assessment data alone or in combination with the patient's activities assessment data, (ii) the patient's bone density assessment data, and (iii) the patient's height and weight into one or more computer generated patient feedback reports via the computer software.

25. The method as claimed in claim 24, further comprising:

collecting physical symptoms assessment data of a patient, wherein the patient's physical symptoms assessment data comprises spine curvature data.

26. The method as claimed in claim 25, wherein the patient's spine curvature data comprises a lumbosacral angle, a L1/T12 score, and a T1/C7 score.

27. The method as claimed in claim 24, wherein the region of interest is the patient's L3 lumbar region.

28. The method as claimed in claim 24, wherein the group of pre-determined tasks are selected from the group of tasks consisting of: a pour task; a footwear task; a newspaper task; a reach-lift task; a sweep task; a washer task; a dryer task; a sit to floor task; a carry-climb task; a night walk task; and any combination thereof.

29. The method as claimed in claim 24, wherein the method comprises the step of collecting activities assessment data of the patient.

* * * * *